United States Patent [19]

Groll et al.

[11] Patent Number: 4,859,412

[45] Date of Patent: Aug. 22, 1989

[54] METHOD OF PRODUCING ALLOYED POWDERS FOR DENTAL AMALGAMS

[76] Inventors: Werner Groll, Gartenstrasse 5, 8755 Alzenau-Hörstein; Doris Hathaway, Lahnstrasse 20, 6450 Hanau 7; Gernot Schöck, Bahnhofstrasse 56, 6454 Bruchköbel, all of Fed. Rep. of Germany

[21] Appl. No.: 197,360

[22] Filed: May 23, 1988

[30] Foreign Application Priority Data

May 21, 1987 [DE] Fed. Rep. of Germany ....... 3717048

[51] Int. Cl.$^4$ ............................................. B22F 1/00
[52] U.S. Cl. ........................................ 419/23; 419/30; 419/33; 419/53; 419/54; 419/68; 420/502
[58] Field of Search ....................... 419/23, 30, 33, 53, 419/54, 68; 420/502

[56] References Cited

U.S. PATENT DOCUMENTS

| | | | |
|---|---|---|---|
| 4,030,918 | 6/1977 | Sung et al. | 75/0.5 R |
| 4,080,199 | 3/1978 | Sung et al. | 75/0.5 R |
| 4,453,977 | 6/1984 | Burns et al. | 75/0.5 R |
| 4,479,823 | 10/1984 | Hohmann | 75/0.5 R |

*Primary Examiner*—Stephen J. Lechert, Jr.
*Attorney, Agent, or Firm*—Cushman, Darby & Cushman

[57] ABSTRACT

An economical alloyed powder for dental amalgams exhibiting good working properties is obtained from pressed and sintered molded bodies by mechanical comminution. The formed body is produced by mixing and pressing powders of elemental silver, copper and tin with a subsequent sintering between 150° C. and the solidus temperature of the alloy being formed. The sintering is performed until a homogeneous distribution of the tin has been achieved in the silver and copper particles.

6 Claims, No Drawings

METHOD OF PRODUCING ALLOYED POWDERS FOR DENTAL AMALGAMS

The present invention relates to alloyed powders for dental amalgams and a method of producing them. The alloys consist of silver, copper, tin and, optionally, additives of indium, zinc, palladium, ceramic powder and/or glass powder. The method includes the steps of mechanically comminuting a pressed and sintered molded body. The powders obtained in this way are triturated with mercury and are used as amalgams for filling dental cavities.

BACKGROUND OF THE INVENTION

Silver amalgams have been used successfully for decades as filling material for teeth damaged by tooth diseases. They are especially useful for this purpose because of their high mechanical strength, long life and ease of use. The amalgam is produced at the dentist's office from a suitable alloyed powder and pure mercury. The alloyed powders normally consist of silver, copper and tin and frequently also of a little zinc. The silver content varies from 24 to 93% by weight (cf. for example published German Patent Specification DE-OS No. 25 11 194 and U.S. Pat. Nos. 3,985,885, 4,039,329, 3,975,192, 4,030,918, 3,762,917 and 3,871,876). Other additives are also used in some cases, such as indium (see e.g. U.S. Pat. No. 4,030,918) or palladium (U.S. Pat. No. 4,374,085).

The alloyed powders are normally produced using molten metallurgical techniques, either by spraying the melt or by machining a cast molded body (e.g. a bar or a billet).

When the spraying process is used, the powder is produced directly from the melt by passing the melt stream through a funnel and then through an annular nozzle loaded with water or gas, after which the stream is atomized. As a result of the high cooling speed which occurs in this process, the particles which are formed are primarily spherical. Also, the alloy phases, e.g. $Ag_3Sn$ and $Cu_3Sn$, are present in a finely distributed fashion. Amalgams with great strength are obtained from such powders, especially in the case of low silver contents. On account of the spherical shape of the powder particles and the associated high bulk density, the amount of mercury required for producing a pasty tamping body is less than in the case of chip amalgams produced by machining; however, the working properties are not optimum since the individual particles slide past each other too easily during tamping and thus escape the tamping pressure. Moreover, the working properties of such so-called "ball amalgams" react in a considerably more sensitive manner to errors in measuring the proportions of alloy particles and mercury than do chip amalgams. Further, the manufacturing cost of the sprayed alloy is high, largely because of the low yield of utilizable powder.

On the other hand, when the alloying powder is made by machining, there are increases and a coarse distribution of the $Ag_3Sn$ and $Cu_3Sn$ phases in the molded body and in the alloyed powder. These arise because of the relatively low cooling speed during the production of the cast bar which is machined. This characteristic has a negative effect on the binding reaction with mercury. The technical properties such as e.g. binding expansion and strength are also adversely affected. In addition, the yield of utilizable powder at 30–50% is very low so that increased costs result due to subsequent grinding processes and any separated waste which occurs. An advantage of the chip amalgams over the ball amalgams is their very good workability.

Published German Patent Specification DE-PS No. 32 40 356 describes a method of producing an amalgam powder which uses sintering technology. First, a sprayed alloyed powder is produced from silver-tin-copper which is subsequently compacted and sintered. The porous, sintered, alloyed molded body is then machined. In this manner, an improvement in the quality of the amalgam is achieved. However, this method has the disadvantage of high production costs, which arise chiefly as a result of the production of the alloyed powder via spraying.

SUMMARY OF THE INVENTION

The object of the present invention is to provide a method of producing alloyed powders for dental amalgams consisting of silver, copper, tin and optionally additives of indium, zinc, palladium, ceramic powder and/or glass powder by means of mechanically comminuting a pressed and sintered molded body which method assures a very fine microstructure of the alloyed powder, can be performed with high yields of utilizable amalgam powder and is thus economical.

In accordance with the present invention these and other objects are achieved by mixing and pressing the elementary metal powders of silver, copper, zinc and, optionally, any additives into a molded body and then sintering it at a temperature between 150° C. and the solidus temperature of the alloy being produced until a homogeneous distribution of the tin has been achieved in the silver and copper particles. After cooling, the alloy is machined to form a powder.

In making the compact, the individual powders are intensively mixed so that an agglomerate-free mixture of powders is produced. This powder mixture is compacted in a suitable mold and press to a green compact and subsequently sintered. Then, the sintered body (bar, billet or the like) is machined e.g. in a milling machine and the required fraction separated off.

The sintering process is preferably performed in two stages. The first stage is performed by heating for 1 to 20 hours at a temperature below the melting point of tin (232° C.) and the second stage at temperatures between 232° C. and the solidus temperature of the alloy being produced until a homogeneous distribution of the tin is achieved in the silver and copper particles.

Metal powders with a particle size smaller than 70 $\mu$m have proven to be especially suitable since they assure a sufficiently fine phase distribution and also make possible a relatively short sintering time in which the entire tin content can diffuse into the copper and silver particles.

An even finer distribution of the individual silver and copper-rich phases is achieved if the powder mixture is subjected to a grinding process (e.g. in a high-speed attritor) before the pressing step. The phase size of the silver and copper-rich particles (primarily $Ag_3Sn$ and $Cu_3Sn$) which can be achieved in this manner is in the range of a few micrometers and is comparable to that of sprayed powders in this respect.

If the grinding process is carried out in air, there is a danger of an elevation of the oxygen concentration in the alloyed powder due to the intensive working of the powder. This has a bad effect on the amalgam properties. Therefore, it is preferable to perform the grinding process under the protection of an inert gas atmosphere.

It is also advantageous to produce the molded body to be machined by means of isostatic pressing.

The selection of sintering temperatures depends on the composition of the particular powder or alloy. As already mentioned, the sintering process is preferably performed in two stages. In the first stage, the pressed green compact is sintered at a temperature below the melting temperature of tin (232° C.) for 1-20 hours to permit all of the elemental tin to diffuse into the silver-copper particles. Then the sintering temperature is raised to a temperature between the melting point of tin and the solidus temperature of the alloy and maintained there until a homogeneous distribution of the tin in the copper and silver particles has been achieved. Since the silver and copper particles do not melt during the one-stage nor during the two-stage sintering, their original particle size remains essentially preserved. A small particle size can be achieved more easily in the production of elementary metal powders than in the production of alloyed powders.

The technical properties of the amalgams produced with the alloyed powders produced in accordance with the invention meet or exceed the requirements of the ADA or ISO specifications, as follows:

| ADA: | Dimensional change during binding: | +2 μm/cm |
|---|---|---|
| | Creep | 3.0% |
| | Resistance to compression after one hour | 80 MPa |
| ISO: | Dimensional change during binding: | −10 to 20 μm/cm |
| | Creep | 3.0% |
| Resistance to compression after one hour | | 50 MPa |
| Resistance to compression after 24 hours | | 300 MPa |

The amalgams exhibit the good workability characteristic of chip amalgams. In some instances, especially in the range of low Ag contents, distinctly better amalgam properties are achieved with the alloyed powders produced in accordance with the invention than with an alloyed powder of the same composition produced with casting technology. The yield of milled powder which exhibits the particle size suitable for the production of amalgam is with 70-85% nearly twice as high compared to amalgam powders produced according to casting technology, so that an expensive grinding of the coarser, milled powder which influences the properties remains limited to very small amounts.

DETAILED DESCRIPTION OF PREFERRED EMBODIMENTS

The following examples are intended to explain the method of the invention in more detail:

EXAMPLE 1

50% silver powder (smaller than 63 μm), 30% tin powder (from the firm - Merck, item No. 7807) and 20% copper powder (smaller than 63 μm) were mixed in a mixer for approximately 15 min., then filled into a tightly closable rubber mold (cylinder) and isostatically pressed at 1000 MPa to a billet. The blank was sintered for eight hours at 300° C. under an atmosphere of argon. According to the results of structural and microprobe tests, none of the elementary powders remained after the sintering. The intermetallic phases $Ag_3Sn$ and $Cu_3Sn$ had been produced by tin having diffused into the silver and copper. After machining in a filing machine, the powder fraction smaller than 63 μm was sieved off and annealed four hours under an inert gas atmosphere ($N_2/H_2=80/20$) at 180° C. The trituration with mercury was performed in a Duomat R (firm - Degussa) with a mixing ratio of alloyed powder to mercury of 1:1.2. The mixing time was 40 seconds. The properties of the amalgam produced with this alloyed powder are given in the table.

EXAMPLE 2

70% silver powder (smaller than 63 μm), 27% tin powder (firm - Merck, item No. 7807) and 3% copper powder (smaller than 63 μm) were mixed in a mixer for approximately 15 min., then filled into a tightly closable rubber mold (cylinder) and isostatically pressed at 1800 MPa to a billet. The blank was sintered for six hours at 300° C. under an atmosphere of argon. According to the results of structural and microprobe tests, none of the elementary powders remained after the sintering. After machining in a filing machine, the powder fraction smaller than 63 μm was sieved off and annealed for four hours under a gas atmosphere ($N_2/H_2=80/20$) at 240° C. Trituration with mercury was performed in a Duomat R (firm - Degussa) with a mixing ratio of alloyed powder to mercury of 1:1.2. The properties of the amalgam produced with this alloyed powder are given in the table.

EXAMPLE 3

Silver powder, copper powder and tin powder with a composition corresponding to that of Example 2 were mixed in the same manner and pressed (800 MPa). The sintering process was performed in two stages. In the first stage, the material was sintered for 6 hours at 230° C. and subsequently it was sintered for 2 hours at 400° C. under an atmosphere of argon. Further production steps were as described in Example 2. The properties of the amalgam are given in the table.

EXAMPLE 4

45% Ag powder (smaller than 20 μm), 24% copper powder (smaller than 20 μm) and 31% tin powder (from the firm - Merck, item No. 7807) were mixed as described in Example 1 and pressed (amount of pressure applied 120 MPa). The sintering was performed as in Example 3 in two stages at the same temperatures, but under an atmosphere of nitrogen and hydrogen ($N_2/H_2=80/20$). The structural tests in a light-optical microscope and in a microprobe showed that the alloy consists of a copper-tin phase and a silver-tin phase which were identified by means of X-ray microstructure investigation as $Ag_3Sn$ and $Cu_3Sn$. The pure original metal powders no longer are found in the structure. The sintered alloy was milled with a solid cylindrical cutter. The yield of powder fraction smaller than 63 μm which could be utilized for the production of amalgam was 82%. The heat treatment of the sieved-out fraction smaller than 63 μm was performed for four hours at 80° C.under an inert gas atmosphere ($N_2/H_2=80/20$). The data of the amalgam produced with this alloyed powder is given in the table. The amalgam is free of $\gamma_2$.

EXAMPLE 5

5% by volume glass powder (≦5 μm) was added to the silver, copper and tin powders corresponding to the composition in Example 4. Mixing, pressing, sintering and milling were performed in a manner which was analogous to Example 4. After the sintering, the glass particles were finely distributed in the matrix of $Cu_3Sn$ and $Ag_3Sn$. The yield during milling was 76%. After the heat treatment of the powder fraction smaller than 63 μm (as in Example 4), the alloyed powder was triturated with mercury. The properties of this amalgam are given in the table.

EXAMPLE 6

A powder mixture corresponding to Example 4 (150 g) was triturated with zirconium oxide balls (600 g) in alcohol in an attritor whose grinding vessel consisted of zirconium oxide and which was water-cooled. The speed was 1200 revs/min., the grinding time being 4 hours. After separation of the grinding medium, the ground powder was filled into a rubber mold and further processed in a manner which was analogous to Example 4. After the sintering, a structure was present in which the $Ag_3Sn$ and $Cu_3Sn$ phases were present in an extremely fine distribution. The phase size was in the range of a few μm.

TABLE

|  | Mixing Ratio Alloy:Hg | Mixing Time (sec) | Creep | Change in Length During Hardening (μm/cm) | Resistance to Compression in MPa after | | |
|---|---|---|---|---|---|---|---|
|  |  |  |  |  | 1 h | 24 h | 7 d |
| Example 1 | 1:1.2 | 40 | 0.45 | +10 | 90 | 340 | 370 |
| Example 2 | 1:1.2 | 30 | 1.6 | −11 | 85 | 290 | 310 |
| Example 3 | 1:1.2 | 30 | 1.2 | −8 | 130 | 330 | 385 |
| Example 4 | 1:1.3 | 30 | 0.22 | +4 | 126 | 385 | 450 |
| Example 5 | 1:1.3 | 30 | 0.25 | +5 | 105 | 330 | 360 |

What is claimed is:

1. A process for the production of alloy powders for dental amalgams from silver, copper, tin and, optionally, additions of indium, zinc, palladium, ceramic powder and/or glass powder by means of mechanical size reduction of a sintered compact, said process comprising mixing and compressing the elemental powders silver, copper, tin and, optionally, additions of indium, zinc, palladium, ceramic and/or glass powder, to form a compact and sintering the compact at a temperature between 150° C. and the solidus temperature of the alloy being produced until a homogeneous distribution of the tin has been achieved in the silver and copper particles.

2. A process as set forth in claim 1 in which the sintering process takes place in two stages, the first stage being performed for 1 to 20 hours at a temperature below the melting point of tin (232° C.) and the second stage at temperatures between 232° C. and the solidus temperature of the alloy being produced, until a homogeneous distribution of the tin has been achieved in the silver and copper particles.

3. A process as set forth in any one of claims 1 and 2 in which the particle size of the powders added is less than 70 μm.

4. A process as set forth in any one of claims 1 and 2 in which the powders are subjected to a grinding process before the pressing.

5. A process as set forth in any one of claims 1 and 2 in which the grinding process is performed under an inert gas atmosphere.

6. A process as set forth in any one of claims 1 and 2 in which the molded body is produced by isostatic pressing.

* * * * *